United States Patent [19]

Polaschegg

[11] Patent Number: 4,834,888

[45] Date of Patent: May 30, 1989

[54] HEMODIALYSIS APPARATUS COMPRISING A STERILE FILTER

[75] Inventor: Hans-Dietrich Polaschegg, Oberursel, Fed. Rep. of Germany

[73] Assignee: Fresenius AG, Fed. Rep. of Germany

[21] Appl. No.: 128,131

[22] Filed: Dec. 3, 1987

[30] Foreign Application Priority Data

Dec. 8, 1986 [DE] Fed. Rep. of Germany ....... 3641843

[51] Int. Cl.$^4$ ............................................ B01D 13/00
[52] U.S. Cl. .................................... 210/646; 210/90; 210/99; 210/130; 210/134; 210/254; 210/258; 210/259; 210/295; 210/321.69; 210/321.72; 210/321.84; 210/409; 210/416.1; 210/433.1; 210/472; 210/741; 210/791; 210/806
[58] Field of Search ................. 210/741, 791, 806, 90, 210/99, 120, 130, 134, 254, 257.2, 258, 259, 295, 321.69, 321.72–321.81, 321.84, 409, 416.1, 420, 433.1, 472; 73/38, 40

[56] References Cited

U.S. PATENT DOCUMENTS 4,267,040 5/1981 Schal ............................. 210/321.65
4,702,829 10/1987 Polaschegg et al. ........... 210/321.72

FOREIGN PATENT DOCUMENTS 2838414 3/1980 Fed. Rep. of Germany .
3444671 6/1986 Fed. Rep. of Germany .

Primary Examiner—W. Gary Jones
Attorney, Agent, or Firm—Townsend and Townsend

[57] ABSTRACT

A hemodialysis apparatus includes a sterile filter whose outlet, which is usually closed, is connected to a line leading to a discharge outlet in wherein a bypass valve is employed which can be opened at predetermined intervals both during treatment and during flushing operations. The sterile filter has a primary chamber and a secondary chamber. When the bypass valve is opened during treatment, dialysis solution flows out of the primary chamber of the sterile filter and flushes the pyrogens and particles disposed on the membranes of the filter into the discharge. No sterilizating filtration of the dialysis solution takes place through the pores of the membrane because the flow resistance present in the adjoining dialyzer, in conjunction with a degree of clogging of the pores, prevents such a flow. A ventilation means may be provided whereby the bypass circuit of the sterile filter can be ventilated. The bypass circuit may also be employed for a pressure retaining test.

10 Claims, 1 Drawing Sheet

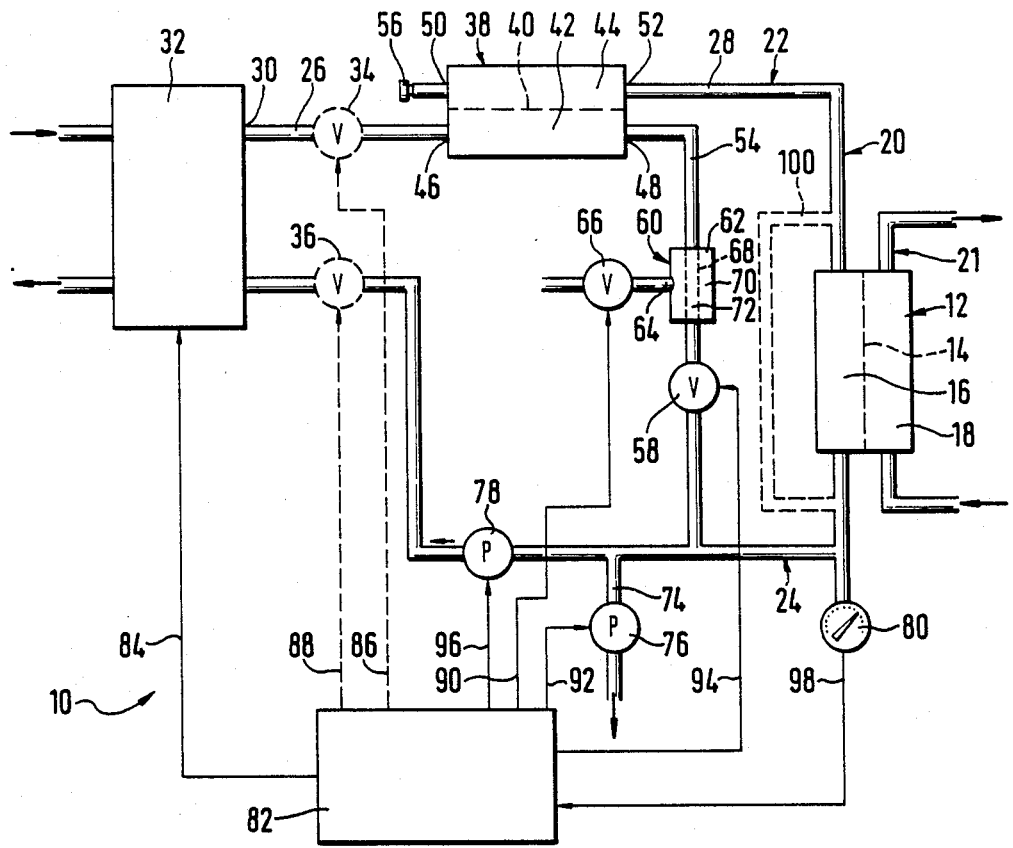

HEMODIALYSIS APPARATUS COMPRISING A STERILE FILTER

BACKGROUND OF THE INVENTION

The invention relates to a hemodialysis apparatus comprising sterilizing means for the dialysis solution, a dialyzer divided by a membrane into two chambers, the first chamber being connected into a dialysis solution path and the second chamber into a blood path, the dialysis solution path comprising a supply line which extends from a means for preparing dialysis solution to the dialyzer and into which a first shutoff member is connected and an exit line which extends from the dialyzer to the discharge and into which a second shutoff member is connected, a pump for conveying the dialysis solution in the dialysis solution path, an ultrafiltration means provided between the shutoff members in the dialysis solution path, a bypass line which connects the supply line to the exit line of the dialysis solution path and into which a bypass valve is connected, and a sterile filter which is divided by a germ-retaining membrane into a first chamber and a second chamber, with a first portion of the supply line of the dialysis solution to the first chamber of the sterile filter and a second portion of the supply line of the dialysis solution from the second chamber of the sterile filter to the dialyzer.

In hemodialysis blood is led along the membrane of a dialyzer, a dialysis solution being led past the other side of the membrane, said solution absorbing through the pores of the membrane the metabolism products to be removed from the blood. In addition, by applying a partial vacuum to the membrane water can be removed from the blood by ultrafiltration.

The dialysis solution is usually prepared on-line from fresh water and an electrolyte concentrate, the latter being inherently sterile and fresh water not usually containing any germs. However, it is not ensured that the dialysis solution thus made is absolutely sterile.

For this reason it has been proposed that upstream of the dialyzer a sterile filter be connected into the dialysis solution path in order to supply an absolutely sterile dialysis solution to the dialyzer.

In similar manner, from the dialysis solution which was not absolutely sterile a completely sterile substitution solution for hemofiltration has been prepared, the substituate line leading from the dialysis solution line including at least one sterile filter. Such systems are described for example in DE-OS No. 3,444,671, EP-OS No. 42,939 and Trans. Am. Soc. Intern. Organs. (ASAIO), Vol. 24 (1978), p. 465–467, and Vol. 25 (1979), p. 404–408.

Hitherto, however, such a sterile filter has been connected into hemodialysis apparatuses only in exceptional cases because the dialysis available at present on the market are restricted in their filtration capacity in that they allow the filtration from the blood side to the dialysis solution side and not conversely.

The development of high-performance dialyzers on the one hand and dialysis apparatuses with ultrafiltration control on the other has led to the possibility of a pressure gradient occurring from the dialysis solution to the blood in hemodialysis and this resulting possibly in backward filtration.

High-performance dialyzers such as the F60 dialyzer of Applicants have a high ultrafiltration coefficient, i.e. only a small transmembrane is required to obtain the fluid extraction usually necessary in the treatment of chronic and acute renal insufficiency.

Modern hemodialysis apparatuses, such as the A2008C apparatus of Applicants, have means for monitoring the fluid withdrawal and it is particularly advantageous that this apparatus permits treatment without fluid withdrawal.

Due to the flow resistances zones arise in the dialyzer in which the pressure in the dialysis solution is greater than the pressure on the blood side. This leads to the aforementioned backward filtration.

Although this phenomenon has been known for years and meanwhile hundreds of thousands of treatments have been carried out without complication, there is the danger that on rupture within a membrane zone of the dialyzer and backward filtration contamination of the blood can occur because the dialysis solution is as a rule not completely sterile.

One step of taking precautions against such a possibility, which as mentioned above cannot be excluded, is to conduct the dialysis solution directly in front of the dialyzer through a filter which retains germs and pyrogens (fever-inducing substances). Admittedly, such a filter can also become defective during the treatment. However, this is of no significance as long as the dialyzer remains intact. The probability that during a treatment both the dialyzer and the sterile filter have a defect is negligibly small. The remaining risk this involves corresponds to the usual risk in hemodialysis. However, an essential point here is the restriction to the time period of a single hemodialysis treatment. This makes it necessary to test the sterile filter regularly before each treatment. If this is not done a filter which is no longer intact may be used for a longer period of time without thish being noticed. Any defect then occurring in the hemodialyzer then automatically endangers the patient. Furthermore, the sterile filter should be operated in as optimum a manner as possible and this requires regular cleaning.

An arrangement of the aforementioned type has however the following disadvantages for routine operation in which the filter is to be used as long as possible.

The so-called "dead end" arrangement of the filter leads to particles and other substances, e.g. pyrogens, collecting in the course of time in front of the filter and possibly clogging the latter. This is dangerous in particular when by a rupture these substances can suddenly be carried into the sterile zone. In this "dead end" arrangement the solution is conveyed by pressure generated upstream into the filter chamber, the entrained germs and pyrogens clogging the pores of the membrane. The arrangement illustrated does not enable the sterile filter to be checked with simple means to ensure that it is intact before each treatment.

The problem underlying the invention is therefore to further develop the dialysis apparatus of the type mentioned at the beginning in such a manner that clogging of the sterile filter with germs or pyrogens during the dialysis treatment is subtantially prevented.

SUMMARY OF THE INVENTION

The solution of this problem is effected in that the outlet of the first chamber of the sterile filter is connected to the bypass line leading to the exit line.

According to the invention the arrangement of a sterile filter is proposed whose outlet, which is usually closed, is connected to the line leading to the discharge. The bypass valve can be opened in predetermined intervals both during the treatment and during the flushing operation of the entire arrangement. When during the treatment the bypass valve is opened the dialysis solution flows out of the primary chamber of the sterile filter and flushes there into the discharge the pyrogens and particles disposed on the membrane. No sterilizing filtration of the dialysis solution takes place through the pores of the membrane because the flow resistance present in the adjoining downstream dialyzer in conjunction with the degree of clogging of the pores prevents such a flow.

After a predetermined flushing period the bypass valve is closed again so that the dialysis treatment can be carried out again.

Furthermore, after each treatment the sterile filter can be automatically flushed with water and disinfection solution and thereafter tested for any rupture.

For this purpose according to a preferred embodiment the sterile filter is again connected into the dialysis solution circuit (the primary side in the so-called bypass circuit and the secondary side in the so-called dialysis solution circuit). Since in each disinfection and flushing operation of the hemodialysis apparatus automatic switching is effected between the bypass and dialysis modes, flushing of the primary side of the sterile filter takes place at regular intervals. Furthermore, the membrane of the sterile filter can be tested in simple manner to ensure that it is intact. The dialysis apparatus is switched to dialysis mode with the bypass valve closed and the bypass line ventilated between the sterile filter and the bypass valve. For this purpose a ventilation means is provided which can be formed for example as a line which branches off the bypass line and the end of which can be sealed with a ventilation valve. Said valve is opened for the ventilation so that only air is then introduced into the circuit because the dialysis solution supply is interrupted. A retaining test can then be carried out on the apparatus thus prepared and this makes it possible to check the intactness of the fluid balancing system of the apparatus and of the sterile filter. In this pressure retaining test fluid is withdrawn from the closed circuit with the aid of the ultrafiltrate pump and said fluid is first expelled from the bypass part by the simultaneously supplied air. The expulsion of the dialysis solution is completed when the entire primary side of the sterile filter is filled with air. Due to its wetting with water the membrane of the sterile filter forms a barrier which is impermeable to air and as a result on further discharge of the dialysis solution on the secondary side of the sterile filter a partial vacuum rapidly builds up which remains stable for a relatively long time even after switching off the ultrafiltrate pump. The pressure value at which the ultrafiltrate pump is switched off can be set at a control unit which swiches off the ultrafiltrate pump when said pressure value is reached and subsequently the time variation of the pressure values followed at a manometer.

Said pressure value will remain substantially stable over a predetermined period if the membrane is intact, i.e. no air can pass through the membrane. If however the membrane has a leak air will flow through and this will lead to a negative result of the pressure retaining test.

Consequently, this pressure retaining test first provides an indication of a defect in the entire balancing system or at the sterile filter. It is then possible in a subsequent second test step to differentiate between these two possibilities by cancelling the ventilation of the sterile filter, i.e. closing the ventilation valve and repeating the test. In such a tep the closed circuit, i.e. the balancing system, is tested in the manner already usual in the A2008C of Applicants.

To positively vent the sterile filter after this test operation, in the primary circuit the solution supply line is advantageously arranged at the bottom and the exit line advantageously at the top. In the secondary circuit either both outlets are connected together or the lower outlet is sealed and only the upper outlet is used.

According to a first embodiment the ventilation of the bypass line necessary for the test can be carried out manually. Advantageously, the venting is effected by a means permitting sterile ventilation of this part of the apparatus to avoid formation of dead zones which are difficult to disinfect.

For this purpose, within a pressure-stable housing a hydrophobic microporous air-permeable membrane is provided and is in flow communication with the bypass line. From the housing itself a vent connecting tube piece leads and the end thereof is sealed with the ventilation valve.

If it is ensured that in the hemodialysis this region always has a positive pressure compared with the environment then said region will always be free of air, i.e. the ventilation valve need not necessarily be provided. In contrast, in the pressure retaining test a partial vacuum is generated which permits the entry of air through the pores of the flexible tube.

If however it is not ensured that an excess pressure is always present in the region of this ventilation means said housing is connected to the aforementioned ventilation valve. During the test this valve is then opened to allow air to flow to the bypass line.

According to a further advantageous embodiment the arrangement is advantageously such that any condensation water forming in the outer space (air space) can flow away when the ventilation valve is opened.

Further advantages of the invention will be explained with reference to an example of embodiment.

BRIEF DESCRIPTION OF THE DRAWINGS

The FIGURE shows schematically a hemodialysis apparatus with sterilizing means for the dialysis solution.

DESCRIPTION OF SPECIFIC EMBODIMENTS

In the FIGURE 10 denotes a hemodialysis apparatus having a conventional dialyzer 12 which is divided by a membrane 14 into a chamber 16 traversed by dialysis solution and a chamber 18 traversed by blood.

The chamber 16 is connected into a dialysis solution path 20 which consists of a supply line 22 and an exit line 24. On the other hand, the chamber 18 is connected into a blood path 21.

As apparent from the FIGURE the supply line 22 consists of a first supply line portion 26 and a second supply line portion 28. The first line portion 26 is connected at its one end to a balance chamber 32 as implemented for example in Applicants' A2008C and described in DE-OS No. 2,838,414, to which express reference is made for reasons of disclosure.

Said balance chamber is separated by a flexible wall, not shown, into two halves, the one half being connected to the supply line 22 and the other half being connected to the exit line 24. Furthermore, for reasons of clarity a second balance chamber has not been shown, said chamber being filled with fresh dialysis solution or flushing or disinfection solution. This filling and emptying operation is indicated by the two arrows shown in the drawing on the left next to the balance chamber. Thus, fresh dialysis solution is accordingly supplied from a dialysis solution source, not shown, to the balance chamber 32 and removed again at the outlet after passing through the dialyzer 12. According to a further embodiment, if a usual single-pass apparatus is employed, instead of the balance chamber 32 a first shutoff valve 34 may be disposed in the supply line 22, in particular in the first supply line portion 26, as illustrated in dashed in line in the FIGURE.

Furthermore, in the exit line 24 a second shutoff valve 36 may be disposed and as a result between the two valves 34 and 36 or between the balance chamber halves of the balance chamber 32 a closed system can be created. Both the balance chamber 32 and the two shutoff valves 34 and 36 represent shutoff members in the sense of the invention.

Connected into the supply line 22 is a sterile filter 38 which comprises a membrane 40 which separates the sterile filter 38 into a first chamber 42 and a second chamber 44. The two chambers 42 and 44 each have connecting means 46 to 52 because advantageously a commercially available sterile filter is used which generally comprises two inlets and two outlets. Thus, in advantageous manner, it is also possible to use as sterile filter a dialysis filter, for example the F60 dialysis filter of Applicants.

The inlet 46 is connected to the other end of the first supply line portion 26. The outlet 48 of the first chamber 42 of the sterile filter 38 is connected to the bypass line 54 whilst the outlet 52 of the second chamber 44 of the sterile filter 38 is connected to the one end of the second supply line portion 28. The other end of the supply line portion 28 is connected in dialysis mode to the input of the first chamber 16 of the dialyzer 12. Finally, the inlet 50 of the second chamber 44 of the sterile filter 38 is sealed with a plug 56.

The membrane 40 of the sterile filter comprises a pore size such that it sterilizes the dialysis solution conveyed therethrough, i.e. retains germs or pyrogens at the membrane surface. For this reason the membrane has a pore size of at the most 0.2 $\mu$m.

The bypass line 54 is connected at its other end to the exit line 24.

Furthermore, a bypass valve 58 is connected into the bypass line 54 and in front of said valve upstream, i.e. in the direction towards the sterile filter 38, a ventilation means 60 is provided.

According to a first embodiment said ventilation means 60 comprises a housing 62 which has at its peripheral surface a connecting tube piece 64 whose end is sealed with a ventilation valve 66. Furthermore, the housing 62 comprises in the interior an advantageously hose-shaped membrane 68 which divides the housing into a first chamber 70 in flow connection with the tube connecting piece 64 and into a second chamber 72 in flow connection with the bypass line 54. The hose-shaped membrane 68 is advantageously made hydrophobic so that no water can penetrate through the pores of the membrane. Furthermore, the membrane 68 is microporous so that no germs can penetrate into the bypass line. For this reason said membrane 68 advantageously has a pore size of 0.2 $\mu$m or less.

From the exit line 24 an ultrafiltrate line 74 branches off and into said line an ultrafiltration pump 76 is connected.

Furthermore, in the extraction line 24 a dialysis solution pump 78 is provided with which the dialysis solution is pumped out of the one balance chamber half into to the other balance chamber half of the balance chamber 32, the flexible wall, not shown, in the balance chamber being correspondingly displaced.

If a dialysis apparatus without balance chambers is used the dialysis solution pump 78 serves to pump the dialysis solution from the dialysis solution source, not shown, through the dialyzer 12 to the discharge.

Finally, the withdrawal line 24 is connected to a manometer 80 so that the pressure obtaining in the dialysis solution path 22 can be determined.

To control the individual components a control unit 82 is provided which is connected via the following control lines to the respective components:

1st control line 84 to the balance chamber 32 or
2nd and 3rd control lines 86 and 88 to the 1st and 2nd shutoff valves 34 and 36,
4th control line 90 to the ventilation valve 66,
5th control line 92 to the ultrafiltrate pump 76,
6th control line 94 to the bypass valve 58,
7th control line 96 to the dialysis solution pump 78.

A signal line 98 goes from the manometer 80 to the control unit 82.

When the hemodialysis apparatus 10 is not being used to treat a patient the dialyzer 12 is removed, whereupon the flushing and disinfection of the apparatus 10 is carried out. For this purpose the supply line 22 and the exit line 24 are removed from the dialyzer and connected together with the aid of a connector 100 as illustrated in dashed line in the drawing. Thus, the two lines are then diretly in flow connection with each other.

As safety means a dialyzer valve, not shown, and upstream thereof a conductivity cell are also connected into the second supply line branch 28 and in response to the signal of said means when an error occurs the bypass valve 58 is opened and the dialyzer valve closed.

The hemodialysis machine shown in the FIGURE is operated as follows during the dialysis.

Via the balance chamber 32 an initially fresh dialysis solution is supplied to the dialyzer 12, this being done with the aid of the dialysis solution pump 78. The dialysis solution is pumped through the first supply line portion 26 into the first chamber 42 of the sterile filter 38, the bypass line first being closed with the aid of the bypass valve 58. By the action of the dialysis solution pump 78 the dialysis solution is drawn through the membrane 40 of the sterile filter 38 and any pyrogens or germs present are retained at the surface of the membrane 40. The dialysis solution thus sterilized passes through the second supply line portion 22 into the first chamber 16 of the dialyzer 12 and from there in a manner known per se into the exit line 24 in which both the ultrafiltration and the separation take place.

To prevent the membrane 40 from becoming clogged by germs or pyrogens at predetermined intervals the control unit 82 sends a signal to the bypass valve via the control line 94, whereupon the bypass valve 58 is opened. Due to the high flow resistance of the dialyzer 12 practically the entire dialysis solution is then conveyed only through the first chamber 42 of the sterile filter 38 into the bypass line 54, the flow of the dialysis solution shearing the germs and pyrogens disposed on the membrane surface away and entraining them with the fluid flow. This cleans the membrane surface. After a predetermined treatment period the control unit 82 again activates the bypass valve 58, i.e. closes said valve, so that the dialysis treatment is started again.

After the dialysis the dialyzer 12 is removed and the two ends of the supply line 22 and the extraction line 24 sealed with a short-circuiting piece 100. A disinfection solution and fresh water are now alternately supplied through the balance chamber 32 for disinfecting and flushing the entire closed system. To clean both parts of the primary and secondary side of the sterile filter 38 the bypass valve 58 is again operated intermittently so that partially only the first chamber 42 is flushed and disinfected and partially also the second chamber 44 is included in the flushing and disinfection step. In this flushing and disinfection phase the ultrafiltration pump 76 is not in operation whilst the dialysis solution pump 78 is. Also, the ventilation valve 66 or the ventilation means 60 are not in operation.

To check the intactness of the sterile filter 38 after the last flushing step the control unit 82 carries out the following control operations:

Firstly, the dialysis solution pump 78 is deactivated so that no supply or discharge of solution takes place. Alternatively, the two shutoff valves 34 and 36 are closed, i.e. a closed system is created. Furthermore, the bypass valve 58 is closed and the ventilation valve 66 is opened. Finally, the ultrafiltration pump 76 is set in operation, the pressure measured at the manometer 80 being observed. Finally, the balance chamber 32 is also deactivated.

Air is now supplied under the action of the ultrafiltrate pumps 76 to the tube connecting piece 64, the interior of the housing 62, i.e. the two chambers 70 and 72, the adjoining bypass line 54 and the first chamber 42 of the sterile filter 38, the solution being forced through the pores of the membrane 40 into the second chamber 44 of the sterile filter 38. As soon as all the solution has been expelled from the first chamber 42 the membrane 40, which is wetted with water, represents a barrier for further penetration of air, assuming that the membrane is intact, i.e. has no tears or ruptures. Thus, for example, a usual sterile filter is impermeable to air at excess pressures of 1.5-3 bar (on the pressure side). A corresponding partial vacuum can be determined with the aid of the manometer 80 and a corresponding signal supplied to the control unit 82 which when a predetermined pressure value is reached deactivates the ultrafiltrate pump 76 and thereupon in time succession registers the pressure values provided by the manometer 80. For a predetermined period of time, for example several minutes, the partial vacuum arising at the manometer 80 remains substantially constant. As soon as a predetermined period of time has passed without substantial change of said pressure values the control unit 82 reports that the sterile filter 38 is intact or requires the user to change the sterile filter 38 and to subject the new filter to a further flushing and disinfection phase.

After the test the entire arrangement is ready for further use.

I claim:

1. Hemodialysis apparatus comprising:
a dialyzer divided by a membrane into two chambers, the first chamber being connected into a dialysis solution path and a second chamber into a blood path, the dialysis solution path comprising:
a supply line which extends from a means for preparing dialysis solution to the dialyzer and into which a first shutoff member is connected and a second exit line which extends from the dialyzer to a discharge and into which a second shutoff member is connected,
a pump for conveying the dialysis solution in the dialysis solution path,
an ultrafiltration means provided between the shutoff members in the dialysis solution path,
a bypass line which connects the supply line to the exit line of the dialysis solution path and into which a bypass valve is connected, and
a sterile filter (38) which is divided by a germ-retaining membrane into a first filter chamber (42) having an inlet (46) and an outlet (48) and a second filter chamber (44), with a first portion of the supply line of the dialysis solution to the first filter chamber of a sterile filter and a second portion of the supply line to the dialysis solution from the second filter chamber of the sterile filter to the dialyzer, wherein the outlet (48) of the first filter chamber (42) of the sterile filter (38) is connected to the bypass line (54) leading to the exit line (24).

2. Apparatus according to claim 1, wherein a ventilation means (60) is connected into the bypass line (54) between the bypass valve (58) and the first filter chamber (42) of the sterile filter (38).

3. Apparatus according to claim 2, wherein the ventilation means (60) comprises a ventilation valve (66).

4. Apparatus according to claim 3, wherein the ventilation means (60) comprises a housing (62) which is connected into the bypass line (54) and comprises in its interior a microporous hydrophobic membrane (68) which divides the interior into a first chamber (70) in flow communication with a tube connecting piece (64) leading from the housing and a second chamber (72) in flow communication with the bypass line (54).

5. Apparatus according to claim 4, wherein the end of the tube connecting piece (64) is connected to the ventilation valve (66).

6. Apparatus according to claim 5, wherein the shutoff means are formed as balance chamber (32) and by a control unit (82) which is connected via a first control line (84) to the balance chamber (32) via a fourth control line (90) to the ventilation valve (66), via a fifth control line (92) to an ultrafiltrate pump (76), via a sixth control line (84) to the bypass valve (58), via a seventh control line (96) to the dialysis solution pump (78) and via a signal line (98) to a manometer (80) used for measuring pressure in an exit line 24.

7. Apparatus according to claim 5, wherein the shutoff means are formed by shutoff valves (36 and 34) and by a control unit (82) which is connected via second and third control lines (86 and 88) to the first and second shutoff valves (36 and 34), via a fourth control line (90) to the ventilation valve (66), via a fifth control line (92) to an ultrafiltrate pump (76), via a sixth control line (84) to the bypass valve (58), via a seventh control line (96) to the dialysis solution pump (78) and via a signal line (98) to the manometer (80).

8. A method for cleaning a sterile filter (38) of a hemodialysis apparatus, said hemodialysis apparatus comprising a dialyzer divided by a membrane into two chambers, the first chamber being connected into a dialysis solution path and a second chamber into a blood path, the dialysis solution path comprising:
a supply line which extends from a means for preparing dialysis solution to the dialyzer and into which a first shutoff member is connected and an exit line which extends from the dialyzer to the discharge and onto which a second shutoff member is connected, a pump for conveying the dialysis solution in the dialysis solution path, an ultrafiltration means provided between the shutoff members in the dialysis solution path, a bypass line which connects the supply line to the exit line of the dialysis solution path and into which a bypass valve is connected, and a sterile filter (38) which is divided by a germ-retaining membrane into a first filter chamber (42) and a second filter chamber (44), with a first portion of the supply line of the dialysis solution to the first filter chamber of the sterile filter and a second portion of the supply line of the dialysis solution from the second filter chamber of the sterile filter to the dialyzer, wherein an outlet (48) of the first filter chamber (42) of the sterile filter (38) is connected to a bypass line (54) leading to an exit line (24), said method comprising the steps of:

opening the bypass valve (58) at predetermined intervals of time during dialysis by means of a control unit (82) in order to bypass said sterile filter; and closing the bypass valve (58) at predetermined intervals of time during dialysis by means of the control unit 82.

9. A method for checking a sterile filter (38) of a hemodialysis apparatus, the hemodialysis apparatus comprising a dialyzer divided by a membrane into two chambers, the first chamber being connected into a dialysis solution path and a second chamber into a blood path, the dialysis solution path comprising:

a supply line which extends from a means for preparing dialysis solution to the dialyzer and into which a first shutoff member is connected and a second exit line which extends from the dialyzer to a discharge and into which a second shutoff member is connected, a pump for conveying the dialysis solution in the dialysis solution path, an ultrafiltration means provided between the shutoff members in the dialysis solution path, a bypass line which connects the supply line to the exit line dialysis solution path and into which a bypass valve is connected, and a sterile filter (38) which is divided by a germ-retaining membrane into a first filter chamber (42) having an outlet (48) and a second filter chamber (44), with a first portion of the supply line of the dialysis solution to the first filter chamber of a sterile filter and a second portion of the supply line to the dialysis solution from the second filter chamber of the sterile filter to the dialyzer, wherein the outlet (48) of the first filter chamber (42) of the sterile filter (38) is connected to the bypass line (54) leading to the exit line (24), wherein a ventilation means (60) is connected into the bypass line (54) between the bypass valve (58) in the first filter chamber (42) of the sterile filter (38), wherein the ventilation means (60) comprises a ventilation valve (66), a housing (62) which is connected into the bypass line (54) and a microporous hydrophobic membrane (68) which divides the interior into a first chamber (70) in flow communication with a tube connecting piece (64) leading from the housing and a second chamber (72) in flow communication with the bypass line (54), wherein the end of the tube connecting piece (64) is connected to the ventilation valve (66), wherein the shutoff means are formed as balance chamber (32) and by a control unit (82) which is connected via a first control line (84) to the balance chamber (32), via a fourth control line (90) to the ventilation valve (66), via a fifth control line (92) to an ultrafiltrate pump (76), via a sixth control line (84) to the bypass valve (58), via a seventh control line (96) to the dialysis solution pump (78) and via a signal line (98) to the manometer (80), said method comprising the steps of:

removing the dialyzer (12), closing the supply (22) and the exit line (24) with a connector (100), deactivating the dialysis solution pump (78) by means of the control unit (82), closing the balance (32) or the shut off valves (34 and 36) by means of the control unit (82), opening the ventilation (60) with respect to the atmosphere by means of the control unit (82), setting the ultrafiltrate pump (76) in operation until a predetermined pressure value is reported by the manometer (80) by means of the control unit (82), thereafter setting the ultrafiltrate pump (76) out of operation by means of the control unit (82), monitoring the pressure value signals furnished by a manometer (80) for a predetermined period of time by means of the control unit (82), and subsequently indicating the intactness of the sterile filter (38) by means of said control unit (82).

10. A method for checking a sterile filter (38) of a hemodialysis apparatus, the hemodialysis apparatus comprising a dialyzer divided by a membrane into two chambers, the first chamber being connected into a dialysis solution path and a second chamber into a blood path, the dialysis solution path comprising:

a supply line which extends from a means for preparing dialysis solution to the dialyzer and into which a first shutoff member is connected and a second exit line which extends from the dialyzer to a discharge and into which a second shutoff member is connected, a pump for conveying the dialysis solution in the dialysis solution path, an ultrafiltration means provided between the shutoff members in the dialysis solution path, a bypass line which connects the supply line to the exit line of the dialysis solution path and into which a bypass valve is connected, and a sterile filter (38) which is divided by a germ-retaining membrane into a first filter chamber (42) having an inlet (46) and an outlet (48) and a second filter chamber (44), with a first portion of the supply line of the dialysis solution to the first filter chamber of a sterile filter and a second portion of the supply line to the dialysis solution from the second filter chamber of the sterile filter to the dialyzer, wherein the outlet (48) of the first filter chamber (42) of the sterile filter (38) is connected to the bypass line (54) leading to the exit line (24), wherein a ventilation means (60) is connected into the bypass line (54) between the bypass valve (58) in the first filter chamber (42) of the sterile filter (38), wherein the ventilation means (60) comprises a ventilation valve (66), a housing (62) which is connected into the bypass line (54) and a microporous hydrophobic membrane (68) which divides the interior into a first chamber (70) in flow communication with a tube connecting piece (64) leading from the housing and a second chamber (72) in flow communication with the bypass line (54), wherein the end of the tube connecting piece (64) is connected to the ventilation valve (66), wherein the shutoff means are formed by shutoff valves (36 and 34) and by a control unit (82) which is connected via second and third control lines (86 and 88) to the first and second shutoff valves (36 and 34), via a fourth control line (90) to the ventilation valve (66), via a fifth control line (92) to an ultrafiltrate pump (76), via a sixth control line (84) to the bypass valve (58), via a seventh control line (96) to the dialysis solution pump (78) and via a signal line (98) to the manometer (80), said method comprising the steps of:

removing the dialyzer (12), closing the supply (22) and the exit line (24) with a connector (100), deactivating the dialysis solution pump (78) by means of the control unit (82), closing the balance (32) or the shut off valves (34 and 36) by means of the control unit (82), opening the ventilation (60) with respect to the atmosphere by means of the control unit (82), setting the ultrafiltrate pump (76) in operation until a predetermined pressure value is reported by the manometer (80) by means of the control unit (82), thereafter setting the ultrafiltrate pump (76) out of operation by means of the control unit (82), monitoring the pressure value signals furnished by a manometer (80) for a predetermined period of time by means of the control unit (82), and subsequently indicating the intactness of the sterile filter (38) by means of said control unit (82).

* * * * *